United States Patent [19]

Matthews et al.

[11] 4,144,397

[45] Mar. 13, 1979

[54] PREPARATION OF 2-ARYL-PROPIONIC ACIDS BY DIRECT COUPLING UTILIZING A MIXED MAGNESIUM HALIDE COMPLEX

[75] Inventors: Gary J. Matthews; Robert A. Arnold, both of Boulder, Colo.

[73] Assignee: Syntex Corporation, Palo Alto, Calif.

[21] Appl. No.: 863,290

[22] Filed: Dec. 19, 1977

Related U.S. Application Data

[63] Continuation-in-part of Ser. No. 769,070, Feb. 16, 1977, abandoned.

[51] Int. Cl.$^2$ ............................................. C07C 51/00
[52] U.S. Cl. .............................. 562/466; 260/346.11; 260/347.3; 562/492; 562/496; 562/602

[58] Field of Search .......... 260/515 R, 515 A, 520 D, 260/346.11, 347.3

[56] References Cited

U.S. PATENT DOCUMENTS

| | | | |
|---|---|---|---|
| 2,290,401 | 7/1942 | Witman | 260/515 R |
| 3,959,364 | 5/1976 | Armitage et al. | 260/515 R |

*Primary Examiner*—Richard Raymond
*Attorney, Agent, or Firm*—Alan M. Krubiner; Joseph I. Hirsch

[57] ABSTRACT

Valuable 2-aryl-propionic acids are prepared by the direct coupling of aryl magnesium bromides with a mixed magnesium halide complex of alpha-bromopropionic acid.

11 Claims, No Drawings

PREPARATION OF 2-ARYL-PROPIONIC ACIDS BY DIRECT COUPLING UTILIZING A MIXED MAGNESIUM HALIDE COMPLEX

RELATED APPLICATIONS

This is a continuation-in-part of our pending application Ser. No. 769,070, filed Feb. 16, 1977, now abandoned.

BACKGROUND OF THE INVENTION

One of the most frequently employed synthetic methods for the preparation of arylalkanoic acids has been the coupling of an aryl organometallic reagent with a haloalkanoic acid derivative such as a haloalkanoic acid ester. This method has proven to be of particular importance for the preparation of the valuable anti-inflammatory agent 2-(6-methoxy-2-naphthyl)propionic acid. In particular, for the preparation of this compound, couplings involving an alpha-halopropionic acid ester and 2-(6-methoxynaphthyl)copper (U.S. Pat. No. 3,658,863), zinc (U.S. Pat. No. 3,663,584) and cadmium (U.S. Pat. Nos. 3,658,858 and 3,694,476) reagents have been utilized. One disadvantage of these procedures is that the organometallic reagent used for the coupling must be prepared from the corresponding Grignard reagent, thus necessitating an additional chemical reaction, additional reagents, and so forth.

In German OLS No. 2145650 the direct coupling of aryl magnesium halides with potassium 2-iodopropionate was described. More recently, in U.S. Pat. No. 3,959,364, it was shown that an improved direct coupling could be effected by reaction of an aryl Grignard reagent with the lithium, sodium, magnesium or calcium salts of 2-bromopropionic acid of the structure $CH_3CH(X)COM$ wherein X is bromo and M stands for OLi, ONa, $O(Mg)_{\frac{1}{2}}$ or $O(Ca)_{\frac{1}{2}}$ (cf. Table II of U.S. Pat. No. 3,959,364). However, it has been found that the preparation of 2-aryl-propionic acids, especially the valuable compound 2-(6-methoxy-2-naphthyl)propionic acid, by this method suffers from a number of inherent disadvantages including preparation of halopropionate salt in the aprotic solvent media that must be employed for the coupling reaction, leading to poor results for large scale preparations.

It would, therefore, be of extreme value to have a coupling process utilizing an aryl Grignard reagent and a suitable halopropionic acid derivative which afforded the desired 2-aryl-propionic acids easily and in reproducible high yield and purity and was readily adaptable to large scale commercial production.

DETAILED DESCRIPTION OF THE INVENTION

The present invention is related to the preparation of known valuable anti-inflammatory agents, more specifically 2-aryl-propionic acids such as 2-(6-methoxy-2-naphthyl)propionic acid which is described in U.S. Pat. No. 3,904,682. More specifically, the present invention concerns a novel process for the preparation of these valuable therapeutic agents.

Still more specifically, the present invention concerns a direct coupling process whereby a desired aryl magnesium bromide is coupled with a mixed magnesium halide complex of alpha-bromopropionic acid, in high yield, to afford the corresponding 2-aryl-propionic acid. All reference to 2-aryl-propionic acids in the specification and the appended claims is to the racemic form of these compounds.

Exemplary of the 2-aryl-propionic acids whose preparation is within the scope of the present invention are those wherein the aryl moiety is 6 methoxy-2-naphthyl, i.e. 2-(6-methoxy-2-naphthyl)-propionic acid;

4-alkylphenyl, wherein "alkyl" refers to straight and branched chain saturated hydrocarbon groups having from one to four carbon atoms, e.g., 2-(4-methylphenyl)propionic acid, 2-(4-isopropylphenyl)propionic acid and 2-(4-isobutylphenyl)propionic acid; and 4'-fluoro-4-biphenyl, i.e., 2-(4'-fluoro-4-biphenyl)propionic acid.

As mentioned above, the prior art U.S. Pat. No. 3,959,364 describes the preparation of arylalkanoic acids by the direct coupling of an aryl Grignard reagent with the Na, Li, $Ca_{\frac{1}{2}}$ and $Mg_{\frac{1}{2}}$ salts of alpha-bromopropionic acid.

It has now been found that, surprisingly, an improved coupling reaction results if one employs, instead of one of the aforementioned salts, a mixed magnesium halide complex of alpha-bromopropionic acid, that is, a species of the formula $CH_3CH(Br)COOMgX$ wherein X is chloro or bromo. In fact, a direct comparison of the magnesium salt of alpha-bromopropionic acid (prepared by both methods disclosed in U.S. Pat. No. 3,959,364) and the novel complex hereof demonstrates a remarkable difference in yield of final products obtained (about a 2-fold difference) and is set forth in further detail in the Examples. It is an additional advantage of the present coupling process that its yields are not affected by the preparation of the mixed magnesium halide complex to the extent the yields of the coupling process of U.S. Pat. No. 3,959,364 are affected by the method of preparation of the 2-bromopropionate salt (cf. U.S. Pat. No. 3,959,364 column 3 lines 10 and 11).

The mixed magnesium halide complex of alpha-bromopropionic acid may be prepared by treatment of the free acid with a suitable Grignard reagent. While the nature of the hydrocarbon moiety of the Grignard reagent is not critical it is preferred that the free hydrocarbon formed in the reaction of alpha-bromopropionic acid with the Grignard reagent does not interfere with the coupling step or workup. As a consequence, Grignard reagents derived from hydrocarbons that are gaseous or liquid at reaction temperatures are particularly suitable, for example alkyl magnesium Grignards with 1 to 12 carbon or aryl magnesium Grignards with 6 to 9 carbon atoms. Specific Grignard reagents that may be employed for this purpose are methyl magnesium chloride, methyl magnesium bromide, ethyl magnesium chloride, ethyl magnesium bromide, isopropyl magnesium chloride, phenyl magnesium chloride, and o-, m-, or p-tolyl magnesium chloride, and the like. Methyl magnesium chloride and methyl magnesium bromide are particularly preferred inasmuch as they are readily commercially available, inexpensive, and lead to the formation of methane gas which escapes from the reaction mixture and does not interfere during reaction or workup. It has been found that, surprisingly, the addition of one of the aforesaid Grignard reagents to alpha-bromopropionic acid results primarily in formation of the aforementioned complex. Addition of the Grignard reagent across the carbonyl moiety of the carboxylic acid, a reaction which normally would be expected to occur to a large degree, appears to be minimal even when a molar excess of Grignard reagent is employed.

Preparation of the mixed magnesium halide complex is normally carried out in an aprotic solvent medium comprising an ether such as diethylether, tetrahydrofuran, 1,2-dimethoxyethane, di-(n-butyl)ether, and the like. The solvent medium may include other aprotic solvents such as aromatic hydrocarbons, e.g., benzene or toluene. A preferred solvent medium for complex preparation is tetrahydrofuran. While the order of addition of reagents is not narrowly critical it is normally preferred to add the Grignard reagent to the alpha-bromopropionic acid. The Grignard reagent, in solution, is preferably from labout 1 to 4 M, most preferably from about 2 to about 3 M. A final complex solution for use in the direct coupling step of from about 1 to about 2 M, preferably from about 1.0 to 1.5 M is desirable. The temperature of the complex formation step is normally maintained between about $-20°$ and $+30°$ C., preferably between about $-10°$ and $+20°$ C.

The coupling reaction itself is suitably performed by contacting a solution of the mixed magnesium halide complex of alpha-bromopropionic acid with the aryl magnesium bromide in an anhydrous aprotic organic solvent medium. Suitable solvent media for the reaction include organic ethers and mixtures of organic ethers with aromatic hydrocarbons as mentioned above for the complex formation step. A particularly preferred solvent medium for the coupling reaction is tetrahydrofuran. It is preferred that the aryl magnesium bromide solution be between 0.5 and 2 M, most preferably about 1.0 M.

The coupling process itself may be carried out over a temperature range of from about $0°$ to about $+100°$ C., preferably between about 10 and $60°$ C. It is particularly preferred to allow the temperature to gradually rise during the addition stage up to about $40°$–$60°$ C. and then to return to ambient temperature until the desired degree of reaction has been attained.

Although the coupling reaction may be conducted utilizing the reagents in varying proportions to one another it is preferred that approximately equimolar amounts of the mixed magnesium halide complex and the aryl Grignard reagent be utilized. Preferred ratios are from about 0.9:1.1 to 1.1:0.9 complex : Grignard reagent.

The reaction may be performed by conveniently contacting the two reagents in the solvent medium in any manner conventional in the art. However, it is particularly preferred to add the mixed magnesium halide complex to the Grignard reagent and to keep these reagents in intimate admixture until the desired reaction is essentially complete.

The time necessary for performance of the desired reaction will, of course, be influenced by the particular choice of reagents, solvents and reaction temperature and will ordinarily be adjusted by the skilled practitioner to allow for the optimum production of the desired product. Generally however such reaction time will be in the range of from about 10 minutes to about 20 hours, usually being in the range of from about 1 to about 5 hours.

After the coupling reaction has proceeded to the desired state of completion the reaction mixture containing the coupling complex ArylCH(CH$_3$)COOMgX is then quenched with a dilute acid, preferably a dilute aqueous mineral acid such as hydrochloric acid or sulfuric acid, in the conventional manner for Grignard reactions. The free 2-aryl-propionic acid product may then be isolated and purified from the quenched reaction mixture by conventional means such as extraction with aqueous alkali (e.g. aqueous sodium or potassium hydroxide), separation of the aqueous alkaline phase from the organic phase and acidification of the aqueous alkaline phase to free the desired acid, which may optionally be extracted into an organic solvent or directly purified in the usual manner such as by washing and/or crystallization.

If desired, the crude reaction product may be directly converted into a pharmaceutically acceptable derivative of the carboxylic acid, such as a salt, ester or amide thereof, or resolved into optical isomers.

The process of the present invention is easily and conveniently performed on a large scale and affords yields of purified product in the 50–75% range.

The following examples are illustrative of the process of the present invention. They are not intended to limit the spirit or scope of the invention in any manner.

PREPARATION 1

Preparation of 2-(6-methoxynaphthyl)magnesium bromide

2-Bromo-6-methoxynaphthalene (23.7 g., 0.1 mole) is dissolved in toluene (30 ml.) and tetrahydrofuran (40 ml.) with heating. This solution is then added over a 10–15 minute period to an excess of magnesium metal (3 g., 0.12 moles), toluene (15 ml.) and tetrahydrofuran (15 ml.) under a nitrogen atmosphere. The reaction mixture is then cooled and stirred for an additional hour at $25°$–$30°$ C. The reaction mixture is then transferred away from the excess magnesium to a clean, dry vessel under nitrogen and stored at $10°$ C. to afford a 1.0 M Grignard reagent.

Proceeding in a similar manner, the Grignard reagent may be prepared using tetrahydrofuran as the sole solvent.

Similarly, by utilizing less solvent, a more concentrated Grignard reagent, e.g., 1.5 M, may be prepared.

PREPARATION 2

Mixed magnesium halide complex of alpha-bromopropionic acid 15.3 G. (0.1 mole) of alpha-bromopropionic acid and 40 ml. of toluene are cooled to $10°$ C. and a solution of 50 ml. of 2 M methylmagnesium bromide in tetrahydrofuran/toluene (1:1) is then added slowly, maintaining the temperature at $10°$–$20°$ C. during the addition time of 15–20 minutes. The reaction mixture is then stirred at $5°$ C. for an additional 20 minutes to afford a 1.1 M solution of the complex.

Proceeding in a similar fashion, the mixed magnesium halide complex may be prepared utilizing tetrahydrofuran as the sole solvent.

Similarly, methylmagnesium bromide may be replaced by other Grignard reagents such as methylmagnesium chloride, isopropylmagnesium chloride, phenylmagnesium chloride, and the like, in concentrations varying from about 1 to about 4 M.

The mixed magnesium chloride complex of alpha-bromopropionic acid (prepared as described above using 3 M CH$_3$MgCl in tetrahydrofuran) was isolated in crystalline form as its tetrahydrofuran monoetherate after distilling tetrahydrofuran from a tetrahydrofuran solution and was analyzed: mp $147°$–$155°$ C.; ir (KBr) 1625, 1450, 1420, 1372, 1291, 1200, 1070, 1030, 988, and 890 cm$^{-1}$; nmr (D$_2$O) delta 1.8 (multiplet, 7) 3.7 (multiplet, 4), and 4.35 ppm (quartet, J=7). Elemental analysis calculated for C$_7$H$_{12}$BrClMgO$_3$: Mg, 8.57%; Cl, 12.49%. Found: Mg, 8.63%, Cl, 12.97%.

PREPARATION 3

Preparation of aryl magnesium bromides 0.025 Moles of aryl bromide is dissolved in tetrahydrofuran (18 ml.). This solution is then added to an excess of magnesium metal (3 g, 0.02 moles), and tetrahydrofuran (7 ml.) under a nitrogen atmosphere. The temperature is maintained at 50°–60° C. with cooling during the addition period of 10–15 minutes. The reaction mixture is then transferred away from the excess magnesium to a clean dry vessel under nitrogen and stored at 10° C. to afford a 1.0 M Grignard reagent. The following Grignard reagents were prepared in this manner:

2-(6-methoxynaphthyl)magnesium bromide
4-(4'-fluorobiphenyl)magnesium bromide
1-(4-isopropylphenyl)magnesium bromide
1-(4-isobutylphenyl)magnesium bromide
1-(4-methylphenyl)magnesium bromide

PREPARATION 4

A. Preparation of the mixed magnesium halide complex of alpha-bromopropionic acid Alpha-bromopropionic acid (3.8 g., 0.025 moles) is dissolved in tetrahydrofuran (8 ml.), and the solution cooled to −10° C. To this solution is added 3 M methylmagnesium chloride in tetrahydrofuran (8 ml.) over a 15-minute period while maintaining the temperature at −10° to 0° C. This affords a 1.1 M molar solution of the complex which is stored at 0° C. or below until use.

Similarly, replacing 3 M methylmagnesium chloride with 1 M methylmagnesium bromide, the corresponding magnesium bromide complex may be prepared.

B. Preparation of the magnesium salt of alpha-bromopropionic acid

Alpha-bromopropionic acid (3.8 g., 0.025 moles) is dissolved in methanol (6 ml.) and the solution is cooled to −10° C. To this is added a 0.5 M magnesium methoxide in methanol solution (25 ml.) over a ten-minute period while maintaining the temperature at −10° to 0° C. Methanol is then removed under reduced pressure to yield the solid salt which is dried in vacuo at 50° C. for twelve hours to yield the dry magnesium salt (4.1 g., 0.0125 moles, purity 97.2%). This salt is dissolved in 19 ml. of tetrahydrofuran for the coupling reaction.

EXAMPLE 1

A. The solution of complex from Preparation 2 is added slowly to the Grignard solution from Preparation 1, maintaining the temperature at 15°–20° C. during the addition time of 10–15 minutes. The reaction mixture is allowed to warm up to room temperature and then stirred for two hours. The reaction mixture is then cooled in an ice bath and a solution of 20 ml. of 12N hydrochloric acid and 150 ml. of water is added. After stirring for 5 minutes, the two-phase system is filtered and the filter cake is washed with 55 ml. of toluene and 50 ml. of water. The organic phase is extracted with 10% potassium hydroxide solution (2 × 150 ml.) and the combined basic extracts are washed with toluene (30 ml.) and neutralized with 12 N hydrochloric acid to pH 1. The white solid 2-(6-methoxy-2-naphthyl)propionic acid is filtered under vacuum and dried at 55° C. in vacuo to afford 15.2 grams (66%), m.p. 149.5°–153.5° C.

B. Alternatively, after filtration, the organic phase may be extracted with 10% potassium hydroxide solution (2 × 150 ml.) which is washed with toluene (30 ml.) and filtered. 15 Ml. of methanol and 12 ml. of toluene are added, then sufficient 12 N hydrochloric acid to bring the pH to between 4 and 5. The resulting slurry is then heated to reflux for 1 hour, cooled and filtered. The precipitate is washed with water (20 ml.) toluene (2 × 3 ml.) and hexane (2 × 3 ml.) and dried at 55° C. in vacuo to yield 15.0 g. (65.1%) of product, m.p. 154.5°–155° C.

EXAMPLE 2

67 Ml. of a 1.5 M solution of the mixed magnesium chloride complex of alpha-bromopropionic acid in tetrahydrofuran (prepared utilizing 3 M methylmagnesium chloride) is slowly added to a cooled (10° C.) solution of 1.5 M 2-(6-methoxynaphthyl)magensium bromide in tetrahydrofuran (67 ml.) at a rate such that the temperature is held at 55° C. or below. The resulting slurry is stirred at 50° C. for one hour and then heated to reflux, allowing 30–40% of the tetrahydrofuran to distill off. The reaction mixture is cooled to 50° C., 30 ml. of toluene is added and the reaction mixture is quenched with aqueous hydrochloric acid and worked up as in Example 1B to afford 2-(6-methoxy-2-naphthyl)propionic acid, m.p. 156°–157° C., in 73% yield.

EXAMPLE 3

A. The magnesium salt of alpha-bromopropionic acid, i.e. [CH$_3$CH(Br)COO]$_2$Mg, was prepared by reacting the acid with ½ molar equivalent of magnesium carbonate, followed by drying the salt at 60° C. in vacuo.

Replacement of the mixed magnesium chloride complex used in Example 2 with this salt resulted in a 34.7% yield of product.

B. The salt of part A was also prepared using ½ molar equivalent of magnesium methoxide, methanol being removed as an azeotrope. Use of the salt in the procedure of Example 2 afforded a 43.0% yield of product.

EXAMPLE 4

Example 3A was repeated, except that ½ molar equivalent of anhydrous magnesium chloride was added to the magnesium salt prior to the coupling reaction. A 5.1% yield of product was obtained.

EXAMPLE 5

The procedure of Example 3B was repeated except that equimolar amounts of alpha-bromopropionic acid and magnesium methoxide were employed. The yield of product obtained was 35.1%.

EXAMPLE 6

Comparative coupling reactions using mixed magnesium halide complexes and Mg½ salts The following coupling reactions, (on the scale indicated below) were carried out utilizing both the mixed magnesium chloride complex of alpha-bromopropionic acid (prepared as in Preparation 4A) or the magnesium salt of alpha-bromopropionic acid (prepared as in Preparation 4B) with the corresponding Grignard reagent (prepared as in Preparation 3). The procedure (illustrated for a 0.025 mole scale) is as follows:

The 1.0 M solution of aryl magnesium bromide is cooled to 10° C. and the solution of either the magnesium salt or magnesium chloride complex in tetrahydrofuran is added over a five-minute period while maintaining the temperature at 10° to 55° C. The reaction mixture is then stirred at 25°–30° C. for two hours. The reaction mixture is then cooled to 10° C. and a solution of 12N hydrochloric acid (10 ml.) and water (50 ml.) is added. Toluene (50 ml.) is then added and the aqueous phase is separated and discarded. The organic phase is extracted twice with 10% potassium hydroxide (50 ml.). The basic extracts are combined and neutralized with hydrochloric acid to give a precipitate which is filtered and dried at 50° C.

The results are presented in the following table:

| Scale (using stoichiometric quantities of reagents) moles of Grignard | Aryl Grignard | $Mg_{\frac{1}{2}}$ salt or MgCl complex | % yield crude (g) | Comments | actual yield |
|---|---|---|---|---|---|
| 0.12 moles | 2-(6-methoxynaphthyl)-magnesium bromide | MgCl | 72.9 (20.1) | product purity = 96.0% | 70% |
| 0.12 moles | 2-(6-methoxynaphthyl)-magnesium bromide | $Mg_{\frac{1}{2}}$ | 43.0 (11.9) | product purity = 86.8% | 37.4% |
| 0.025 moles | 4-(4'-fluorobiphenyl)-magnesium bromide | MgCl | 60.6 (3.7) | m.p. 136–142° C. NMR O.K. | ≈60% |
| 0.025 moles | 4-(4'-fluorobiphenyl)-magnesium bromide | $Mg_{\frac{1}{2}}$ | 28.6 (1.75) | m.p. 130–138° C. | <28% |
| 0.05 moles | 1-(4-isopropylphenyl)-magnesium bromide | MgCl | 55.2 (5.3) | NMR O.K. m.p. 58–64° C. | ≈55% |
| 0.05 moles | 1-(4-isopropylphenyl)-magnesium bromide | $Mg_{\frac{1}{2}}$ | 52.0 (5.0) | product about 50% pure by NMR - oil | ≈26% |

It can be seen from the above, that in each instance a higher yield (approximately 2-fold) of greater purity product was obtained from the mixed magnesium chloride complex.

In a similar manner, comparable results may be achieved for the preparation of the following 2-arylpropionic acids:
2-(4-isobutylphenyl)propionic acid;
2-(4-methylphenyl)propionic acid.

If the above procedure is interrupted prior to quenching with aqueous acid, and the solvent is removed in vacuo, the coupled magnesium halide complexes, ArylCH(CH₃)COOMgX or etherates thereof may be isolated.

The mixed magnesium chloride complex of 2-(6-methoxy-2-naphthyl)propionic acid as its tetrahydrofuran monoetherate (98.1% purity) exhibits the following properties:
m.p. 113° C. (dec.); ir (KBr disc) 1600, 1450, 1410, 1260, 1210, 1155, 1025, 923, 885, 850, 805 and 750 cm$^{-1}$; nmr (DMSO-d₆) delta (TMS) 1.4 (doublet, 2H), 1.8 (multiplet, 4H), 3.6 (multiplet, 5H), 3.9 (singlet, 3H), 7.5 (multiplet, 6H) ppm.

What is claimed is:

1. A process for the preparation of a 2-arylpropionic acid wherein aryl is selected from the group consisting of 6-methoxy-2-naphthyl, 4-alkylphenyl and 4'-fluoro-4-biphenyl which process comprises:
   (a) contacting a solution of an aryl magnesium bromide with a solution of a complex, CH₃CH(Br)COOMgX, wherein X is chloro or bromo, in an aprotic organic solvent medium comprising an ether, and
   (b) quenching the reaction mixture from (a) with acid.

2. The process of claim 1 wherein said solvent medium comprises tetrahydrofuran.

3. The process of claim 1 wherein said step (a) is performed at a temperature between about 10 and 60° C.

4. The process of claim 1 wherein said aryl magnesium bromide solution is between about 0.5 and 2.0 molar and said complex solution is between about 1.0 and 2.0 molar.

5. The process of claim 1 wherein said CH₃CH(Br)COOMgX is prepared by treatment of alpha-bromopropionic acid with a Grignard reagent in an aprotic organic solvent comprising an ether.

6. The process of claim 5 wherein said Grignard reagent is methyl magnesium chloride or methyl magnesium bromide.

7. The process of claim 1 wherein said 2-arylpropionic acid is 2-(6-methoxy-2-naphthyl)propionic acid.

8. The process of claim 1 wherein said 2-arylpropionic acid is 2-(4'-fluoro-4-biphenyl)propionic acid.

9. The process of claim 1 wherein said 2-arylpropionic acid is 2-(4-isopropylphenyl)propionic acid.

10. The process of claim 1 wherein said 2-arylpropionic acid is 2-(4-isobutylphenyl)propionic acid.

11. A process for the preparation of 2-(6-methoxy-2-naphthyl)propionic acid which process comprises:
   (a) contacting an approximately 0.5 to 2.0 molar solution of 2-(6-methoxynaphthyl)magnesium bromide in tetrahydrofuran with an approximately 1.0 to 2.0 molar solution of alpha-bromopropionic acid mixed magnesium chloride or bromide complex in tetrahydrofuran, at a temperature between about 0° and 100° C., and
   (b) quenching the reaction mixture from step (a) with acid.

* * * * *